United States Patent
Thakur et al.

(10) Patent No.: US 10,194,820 B2
(45) Date of Patent: Feb. 5, 2019

(54) METHOD AND APPARATUS FOR DETECTING ATRIAL TACHYARRHYTHMIA USING HEART SOUNDS

(71) Applicant: Cardiac Pacemakers, Inc., St. Paul, MN (US)

(72) Inventors: Pramodsingh Hirasingh Thakur, Woodbury, MN (US); Qi An, Blaine, MN (US); Barun Maskara, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 431 days.

(21) Appl. No.: 14/717,342

(22) Filed: May 20, 2015

(65) Prior Publication Data

US 2015/0342492 A1    Dec. 3, 2015

Related U.S. Application Data

(60) Provisional application No. 62/006,446, filed on Jun. 2, 2014.

(51) Int. Cl.
*A61B 5/04*        (2006.01)
*A61B 5/0464*    (2006.01)
(Continued)

(52) U.S. Cl.
CPC ............ *A61B 5/0464* (2013.01); *A61B 5/024* (2013.01); *A61B 5/0245* (2013.01);
(Continued)

(58) Field of Classification Search
CPC ..... A61B 5/0464; A61B 5/024; A61B 5/0245; A61B 5/04012; A61B 5/0402;
(Continued)

(56) References Cited

U.S. PATENT DOCUMENTS 6,491,639 B1    12/2002    Turcott
6,643,548 B1    11/2003    Mai et al.
(Continued)

FOREIGN PATENT DOCUMENTS

| CN | 106456023 A | 2/2017 |
|---|---|---|
| WO | WO-2015088695 A1 | 6/2015 |
| WO | WO-2015187365 A1 | 12/2015 |

OTHER PUBLICATIONS

Thakur, Pramodsingh Hirasingh, et al, "System and Methods for Detecting Atrial Tachyarrhythmia Using Hemodynamic Sensors", U.S. Appl. No. 62/004,481, filed May 29, 2014.
(Continued)

*Primary Examiner* — Lindsey G Wehrheim
(74) *Attorney, Agent, or Firm* — Schwegman Lundberg & Woessner, P.A.

(57) ABSTRACT

A cardiac rhythm management system senses a cardiac signal indicative of heartbeats and an acoustic signal indicative of heart sounds and detects atrial tachyarrhythmia based on the sensed cardiac and acoustic signals. In various embodiments, the system senses the cardiac and acoustic signals without using an atrial lead, thus allowing for, for example, monitoring atrial fibrillation burden in a heart failure patient who does not wear an implantable device with an atrial lead. In various embodiments, the system detects heartbeats and heart sounds, measures parameters associated with the detected heartbeats and heart sounds, and detects one or more specified types of atrial tachyarrhythmia using the measured parameters. In various embodiments, the measured parameters are selected from heart rate, heart sound amplitude, cycle length variability, and systolic and diastolic intervals.

20 Claims, 10 Drawing Sheets

(51) Int. Cl.

| | | |
|---|---|---|
| A61B 7/04 | (2006.01) | |
| A61B 5/0245 | (2006.01) | |
| A61B 5/00 | (2006.01) | |
| A61B 7/00 | (2006.01) | |
| A61B 5/024 | (2006.01) | |
| A61B 5/0402 | (2006.01) | |
| A61N 1/372 | (2006.01) | |
| A61N 1/362 | (2006.01) | |
| A61N 1/365 | (2006.01) | |
| A61B 5/046 | (2006.01) | |

(52) U.S. Cl.
CPC ........ *A61B 5/0402* (2013.01); *A61B 5/04012* (2013.01); *A61B 5/686* (2013.01); *A61B 5/7275* (2013.01); *A61B 7/00* (2013.01); *A61B 7/04* (2013.01); *A61N 1/365* (2013.01); *A61N 1/3624* (2013.01); *A61N 1/3627* (2013.01); *A61N 1/36578* (2013.01); *A61N 1/37282* (2013.01); *A61B 5/046* (2013.01)

(58) Field of Classification Search
CPC ....... A61B 5/686; A61B 5/7275; A61B 5/046; A61B 7/00; A61B 7/04; A61N 1/3624; A61N 1/3627; A61N 1/365; A61N 1/36578; A61N 1/37282
See application file for complete search history.

(56) References Cited

U.S. PATENT DOCUMENTS

| | | | |
|---|---|---|---|
| 7,853,327 B2 | 12/2010 | Patangay et al. | |
| 2004/0230129 A1* | 11/2004 | Haefner | A61B 17/3206 |
| | | | 600/510 |
| 2007/0142866 A1 | 6/2007 | Li | |
| 2007/0149890 A1 | 6/2007 | Li et al. | |
| 2009/0043218 A1 | 2/2009 | Warner et al. | |
| 2010/0198285 A1 | 8/2010 | Rom | |
| 2010/0241180 A1 | 9/2010 | Whitman et al. | |
| 2010/0331903 A1 | 12/2010 | Zhang et al. | |
| 2011/0224555 A1 | 9/2011 | Park | |
| 2012/0271186 A1 | 10/2012 | Siejko et al. | |
| 2013/0237872 A1* | 9/2013 | Zhang | A61B 5/686 |
| | | | 600/513 |
| 2015/0342466 A1 | 12/2015 | Thakur et al. | |

OTHER PUBLICATIONS

"U.S. Appl. No. 14/698,007, Non Final Office Action dated Apr. 14, 2017", 7 pgs.

"U.S. Appl. No. 14/698,007, Response filed Mar. 6, 2017 to Restriction Requirement dated Jan. 6, 2017", 11 pgs.

"U.S. Appl. No. 14/698,007, Restriction Requirement dated Jan. 6, 2017", 6 pgs.

"International Application Serial No. PCT/US2015/031703, International Preliminary Report on Patentability dated Dec. 15, 2016", 10 pgs.

"International Application Serial No. PCT/US2015/31703, International Search Report dated Sep. 22, 2015", 4 pgs.

"International Application Serial No. PCT/US2015/31703, Written Opinion dated Sep. 22, 2015", 8 pgs.

"U.S. Appl. No. 14/698,007, Notice of Allowance dated Jan. 18, 2018", 5 pgs.

"U.S. Appl. No. 14/698,007, Notice of Allowance dated Sep. 8, 2017", 5 pgs.

"European Application Serial No. 15727196.6, Response filed Aug. 2, 2017 to Communication Pursuant to Rules 161(2) and 162 EPC dated Jan. 27, 2017", 7 pgs.

* cited by examiner

METHOD AND APPARATUS FOR DETECTING ATRIAL TACHYARRHYTHMIA USING HEART SOUNDS

CLAIM OF PRIORITY

This application claims the benefit of priority under 35 U.S.C. § 119(e) of U.S. Provisional Patent Application Ser. No. 62/006,446, filed on Jun. 2, 2014, which is herein incorporated by reference in its entirety.

CROSS REFERENCE TO RELATED APPLICATIONS

This application is related to commonly assigned, Provisional U.S. Patent Application No. 62/004,481, entitled "SYSTEM AND METHODS FOR DETECTING ATRIAL TACHYARRHYTHMIA USING HEMODYNAMIC SENSORS", filed on May 29, 2014, which is hereby incorporated by reference in its entirety.

TECHNICAL FIELD

This document relates generally to cardiac rhythm management and particularly to detecting atrial tachyarrhythmia using a patient's heart rate and heart sounds.

BACKGROUND

The heart is the center of a person's circulatory system. It includes an electromechanical system performing two major pumping functions. The left side of the heart draws oxygenated blood from the lungs and pumps it to the organs of the body to supply their metabolic needs for oxygen. The right side of the heart draws deoxygenated blood from the body organs and pumps it to the lungs where the blood gets oxygenated. These pumping functions result from contractions of the myocardium (cardiac muscles). In a normal heart, the sinoatrial (SA) node, the heart's natural pacemaker, generates electrical impulses, called action potentials, that propagate through an electrical conduction system to various regions of the heart and excite the myocardial tissues of these regions. Coordinated delays in the propagations of the action potentials in a normal electrical conduction system cause the various portions of the heart to contract in synchrony and result in efficient pumping function.

A blocked or otherwise damaged electrical conduction system causes irregular contractions of the myocardium, a condition generally known as arrhythmia. Arrhythmia reduces the heart's pumping efficiency and hence diminishes the blood flow to the body. A deteriorated myocardium has decreased contractility, also resulting in diminished blood flow. A heart failure patient usually suffers from both a damaged electrical conduction system and a deteriorated myocardium. For example, a large percentage of heart failure patients also experience atrial fibrillation (AF), which may affect effectiveness of therapies treating heart failure. To improve efficacy of heart failure therapies, there is a need for monitoring incidence of AF in heart failure patients.

SUMMARY

A cardiac rhythm management system senses a cardiac signal indicative of heartbeats and an acoustic signal indicative of heart sounds and detects atrial tachyarrhythmia based on the sensed cardiac and acoustic signals. In various embodiments, the system senses the cardiac and acoustic signals without using an atrial lead, thus allowing for, for example, monitoring atrial fibrillation burden in a heart failure patient who does not wear an implantable device with an atrial lead. In various embodiments, the system detects heartbeats and heart sounds, measures parameters associated with the detected heartbeats and heart sounds, and detects one or more specified types of atrial tachyarrhythmia using the measured parameters. In various embodiments, the measured parameters are selected from heart rate, heart sound amplitude, cycle length variability, and systolic and diastolic intervals.

In one embodiment, acardiac rhythm management system includes a cardiac sensing circuit, an acoustic sensor, a beat detector, a heart sound detector, a measurement circuit, and an atrial tachyarrhythmia detector. The cardiac sensing circuit is configured to sense a cardiac signal indicative of heartbeats. The acoustic sensor is configured to sense an acoustic signal indicative of heart sounds. The beat detector is configured to detect the heartbeats using the cardiac signal. The heart sound detector is configured to detect at least one specified type heart sound for each beat of the detected heartbeats. The measurement circuit is configured to measure parameters associated with the each beat and the at least one specified type heart sound detected for the each beat. The atrial tachyarrhythmia detector is configured to detect atrial tachyarrhythmia using the measured parameters.

In one embodiment, a method for operating an implantable medical device is provided. A cardiac signal indicative of heartbeats is sensed by the implantable medical device. An acoustic signal indicative of heart sounds is sensed by an implantable acoustic sensor coupled to the implantable medical device. The heartbeats are detected using the cardiac signal by the implantable medical device. At least one specified type heart sound is detected for each beat of the detected heartbeats by the implantable medical device. Parameters associated with the each beat and the at least one specified type heart sound detected for the each beat are measured by the implantable medical device. Atrial tachyarrhythmia is detected using the measured parameters by the implantable medical device.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
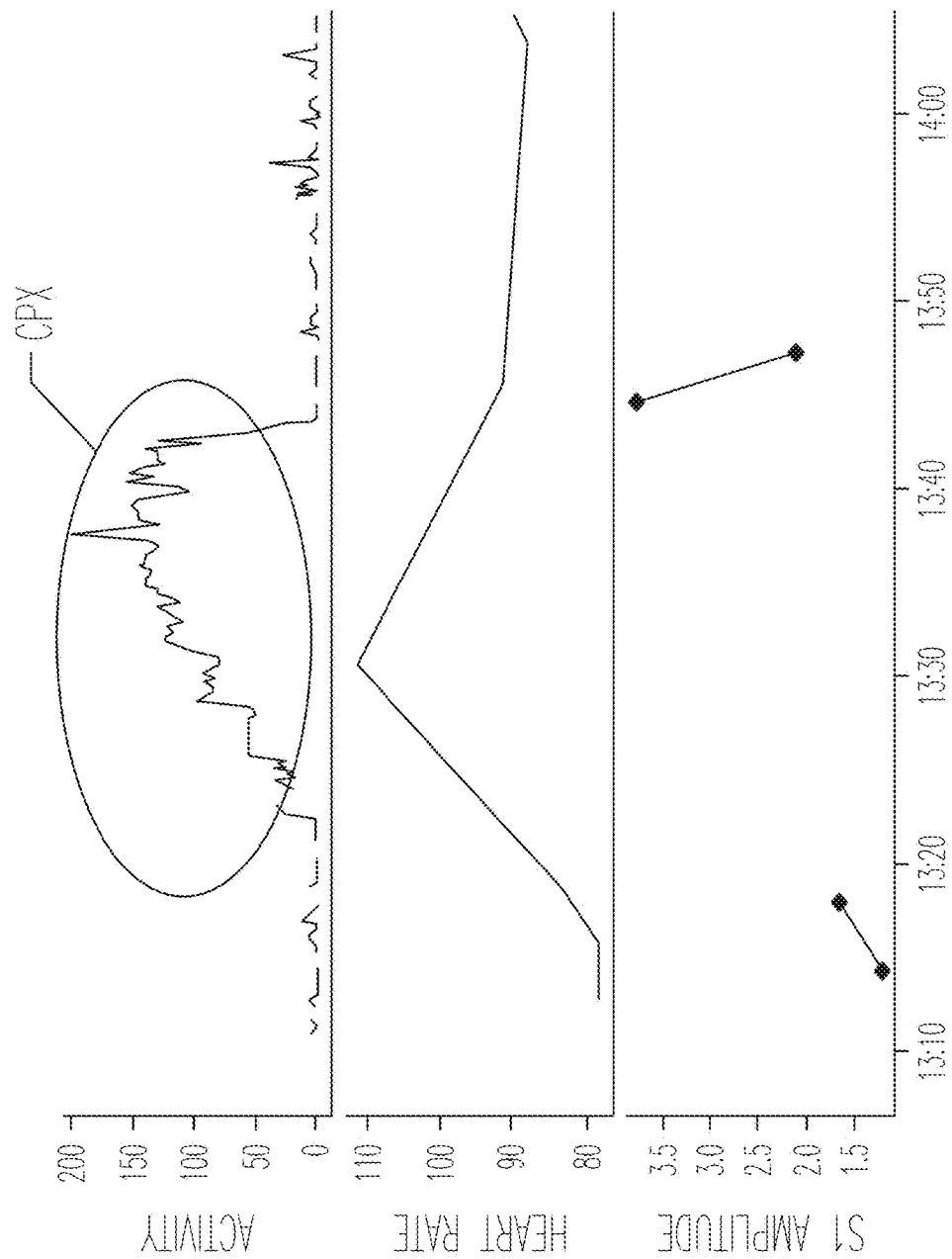
FIG. 1 presents graphs showing increased heart rate and increased first heart sound (S1) amplitude resulting from increased adrenergic state.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this disclosure are not necessarily to the same embodiment, and such references contemplate more than one embodiment.

This document discusses, among other things, a cardiac rhythm management (CRM) system that allows for detection of atrial tachyarrhythmia without using an atrial lead. In one example, the CRM system allows for accurate assessment of atrial fibrillation (AF) for a heart failure patent without requiring implantation of one or more intracardiac leads for this purpose. AF burden is the percentage of time during which a person is in AF. Many heart failure patients are also AF patients. Accurate monitoring of AF burden in these patients will improve efficacy of therapies for heart failure and/or AF, for example, by allowing for more effective titration of medication. An implantable loop recorder, which is configured to be implanted just underneath the skin in a patient's chest, allow for monitoring of the patient's cardiac electrical activities without placing an electrode in or on the heart. However, when being used to monitor incidences of AF, the implantable loop recorder may suffer from practical issues such as muscular noises that render the detection of AF unreliable. The present system provides for accurate assessment of AF burden based on detection of atrial arrhythmias using disassociation between a patient's heart rate and heart sounds during atrial tachyarrhythmia.

Known and studied heart sounds include the "first heart sound" or S1 the "second heart sound" or S2, the "third heart sound" or S3, the "fourth heart sound" or S4, and their various sub-components. S1 is known to be indicative of, among other things, mitral valve closure, tricuspid valve closure, and aortic valve opening. S2 is known to be indicative of, among other things, aortic valve closure and pulmonary valve closure. S3 is known to be a ventricular diastolic filling sound often indicative of certain pathological conditions including heart failure. S4 is known to be a ventricular diastolic filling sound resulted from atrial contraction and is usually indicative of pathological conditions. The term "heart sound" hereinafter refers to any heart sound (e.g., S1) and any components thereof (e.g., M1 component of S1, indicative of Mitral valve closure).

In this document, "heart sound" includes audible and inaudible (subaudible) mechanical vibrations caused by cardiac activity that can be sensed with an accelerometer. In other words, "heart sound" includes cardiac mechanical vibrations in audible and subaudible frequency ranges. Accordingly, when a vibration sensor such as an accelerometer or microphone is used to sense the heart sounds, the scope of energy included in the sensed "acoustic signal" extends to energies associated with such cardiac mechanical vibrations. Unless noted otherwise, S1 refers to the first heart sound, S2 refers to the second heart sound, S3 refers to the third heart sound, and S4 refers to the fourth heart sound, each as a heart sound type, or as one or more occurrences of the corresponding type heart sounds, depending on the context.

The relationship between a heart rate and a cardiac cycle length (also known as cardiac interval), as used in this document, is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, a heart higher than a rate threshold is equivalent to a cycle length (e.g., R-R interval, which is the time interval between two consecutively detected R-waves) lower that a threshold interval. The appended claims should be construed to cover such variations.

In this document, "atrial tachycardia" includes sinus tachycardia and atrial tachyarrhythmia. "Atrial tachyarrhythmia" includes atrial fibrillation (AF) and atrial flutter.

In various embodiments, the present system detects atrial tachyarrhythmia by detecting one or more relationships between the patient's heart rate and a heart sound parameter that is altered during an episode of the atrial tachyarrhythmia. For example, amplitude of the first heart sound (S1 amplitude) is known to be correlated to contractility of the heart in a patient. Under normal conditions, a rise in the patient's heart rate due to increased adrenergic state (such as exercise) is likely to be associated with a rise in the S1 amplitude. When AF or atrial flutter occurs, however, the S1 amplitude decreases when the heart rate increases. The shorter R-R intervals in a non-adrenergic state lead to substantially reduced preload and hence lower contractility (known as Frank-Starling mechanism) and the S1 amplitude. Such relationship between the heart rate (or interval) and heart sound parameters (such as the S1 amplitude) allows for detection of atrial tachyarrhythmia using the heart rate (or interval) and heart rate parameter(s) in the present system.

FIG. 1 presents graphs showing increased heart rate and increased first heart sound (S1) amplitude resulting from increased adrenergic state. A patient's activity is monitored using an accelerometer during a cardiopulmonary exercise (CPX) test. The patient's heart rate and S1 amplitude are measured at several points. The result of the test as illustrated in FIG. 1 shows that both heart rate and S1 amplitude increase and decrease with the patient's level of activity.

Figure 2:
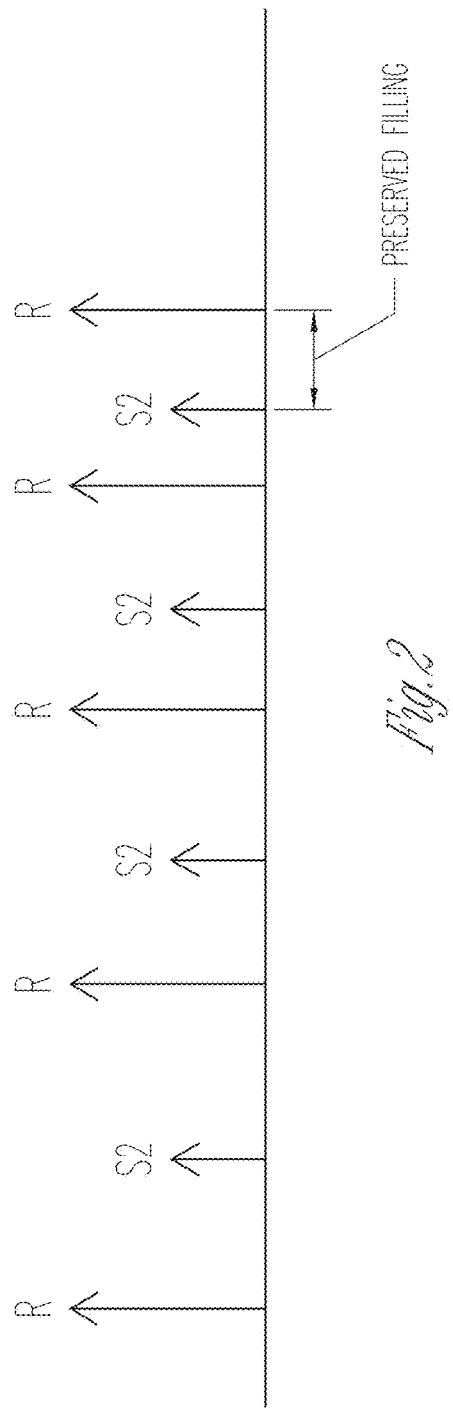
FIG. 2 is a timing diagram illustrating sinus tachycardia with preserved filing.

FIG. 2 is a timing diagram illustrating sinus tachycardia with preserved filing. The timing diagram shows R-waves (ventricular depolarizations) and S2. (the second heart sounds) during SA driven heart rate increase as a result of increased adrenergic state. The time interval between each R-wave and the subsequently adjacent S2 is the systolic interval. The time interval between each S2 and the subsequently adjacent R-wave is the diastolic interval. During an SA-driven tachycardia, preserved filling is indicated by the diastolic intervals which are proportionally shortened in response to heart rate increase and are sufficiently long to allow for adequate filling of the ventricles before systole.

Figure 3:
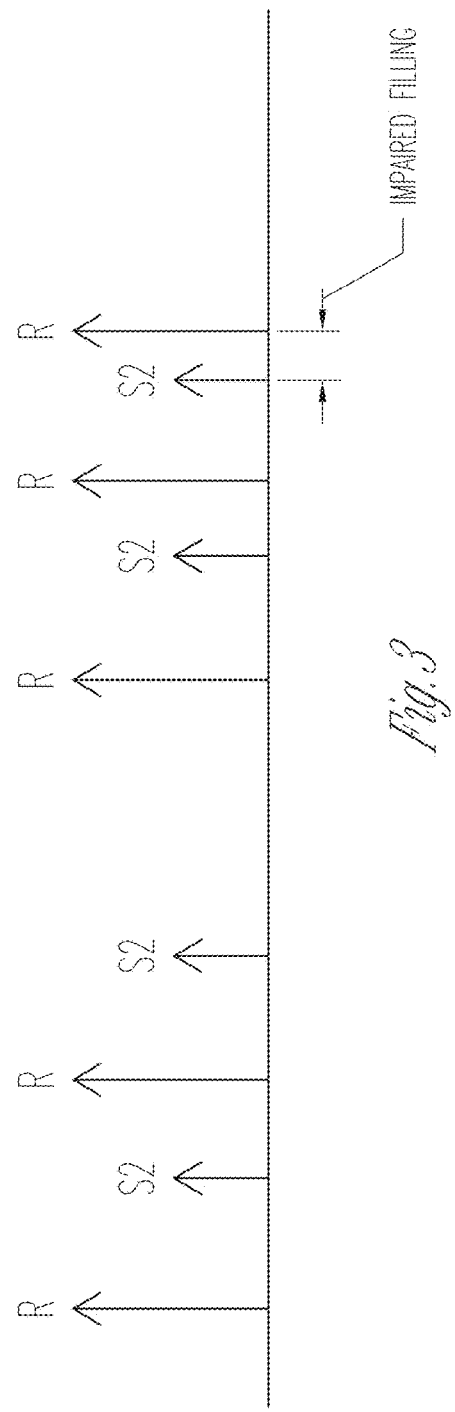
FIG. 3 is a timing diagram illustrating atrial fibrillation (AF) with impaired filing.

FIG. 3 is a timing diagram illustrating atrial fibrillation (AF) with impaired filing. During AF, impaired filling is indicated by irregular diastolic intervals that are disproportionally shortened in response to heart rate increase and are therefore too short to allow for adequate filling of the ventricles before systole.

Figure 4:
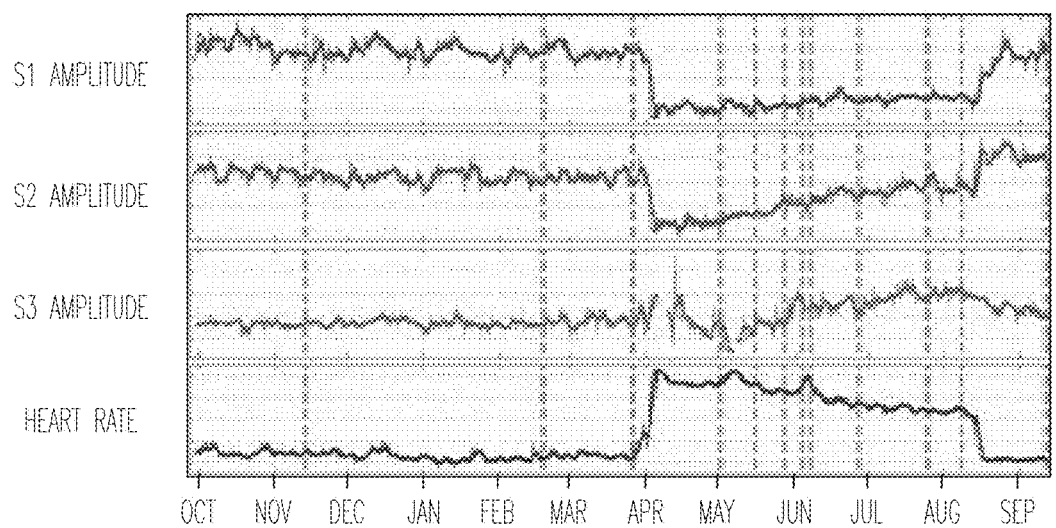
FIG. 4 presents graphs showing an example of a patient's heart rate and heart sound amplitudes during atrial tachyarrhythmia.

FIG. 4 presents graphs showing an example of a patient's heart rate and heart sound amplitudes during atrial tachyarrhythmia. The patient's increased heart rate corresponds to decreased S1 amplitude, decreased S2 amplitude, and increased S3 amplitude.

Figure 5:
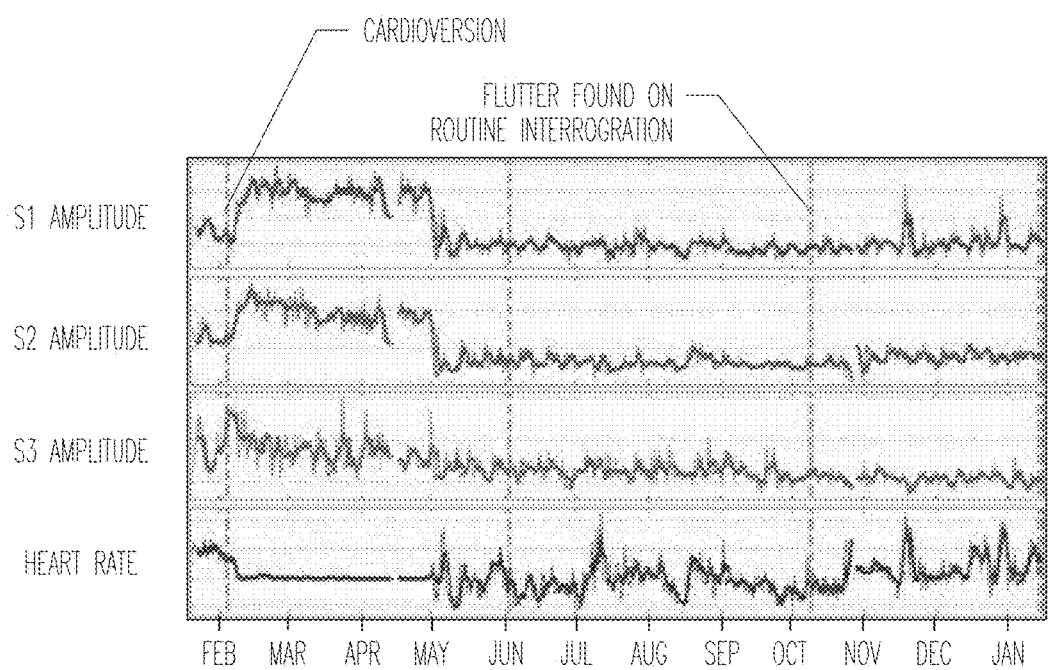
FIG. 5 presents graphs showing another example of a patient's heart rate and heart sound amplitudes during atrial tachyarrhythmia.

FIG. 5 presents graphs showing another example of a patient's heart rate and heart sound amplitudes during atrial tachyarrhythmia. A cardioversion results in the patient's stable heart rate for a certain period associated with increased S1 and S2 amplitudes. A subsequent atrial flutter results in unstable heart rate with decreased S1 and S2 amplitudes.

Figure 6:
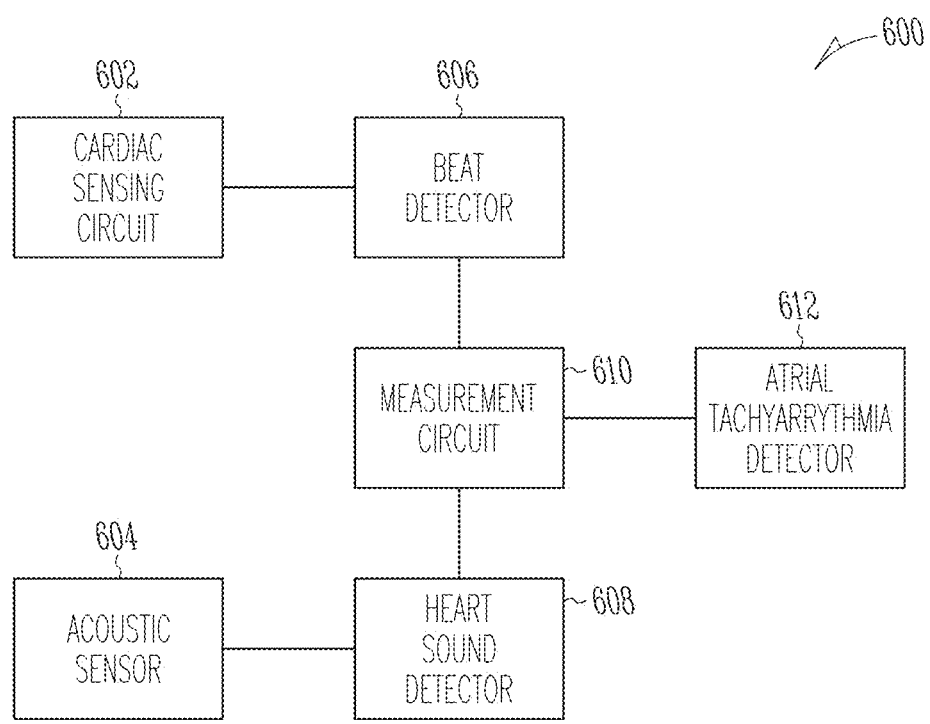
FIG. 6 is a block diagram illustrating an embodiment of a system for detecting atrial tachyarrhythmia using heart sounds.

FIG. 6 is a block diagram illustrating an embodiment of a system 600 for detecting atrial tachyarrhythmia using heart sounds. System 600 includes a cardiac sensing circuit 602, an acoustic sensor 604, a beat detector 606, a heart sound detector 608, a measurement circuit 610, and an atrial tachyarrhythmia detector 612.

Cardiac sensing circuit 602 senses a cardiac signal indicative of heartbeats. A heartbeat includes a complete cardiac cycle. Examples of the cardiac signal include an electrocardiogram (ECG) and an intracardiac electrogram. Acoustic sensor 604 senses an acoustic signal indicative of heart sounds. Examples of acoustic sensor 604 include an accelerometer and a microphone. Beat detector 606 detects the heartbeats using the cardiac signal. In one embodiment, beat detector 606 detects R-waves (ventricular depolarizations) as indications for the heartbeats. Heart sound detector 608 detects at least one specified type heart sound for each beat of the detected heartbeats using the acoustic signal. In various embodiments, heart sound detector 608 is configured to detect S1, S2, S3, or any combination S1, S2, and S3. In one embodiment, heart sound detector 608 is configured to detect at least one specified type heart sound for each beat of the detected heartbeats using ensemble averaging of the acoustic signal.

Measurement circuit 610 measures parameters associated with each beat of the detected heartbeats and the specified type heart sound detected for that beat. In various embodiments, depending on how atrial tachyarrhythmia detector 612 is configured to operate, parameters to be measured include a heart rate associated with each detected beat, an R-R variability, one or more heart sound amplitudes, systolic interval, and diastolic interval. The R-R variability (also referred to as cycle length variability) corresponds to heart rate variability (HRV) measured over a relatively short period. In one embodiment, measurement circuit 610 measures the R-R intervals each associated with a detected R-wave, and determines the R-R variability as the beat-to-beat variance in the R-R intervals over a specified number of heart beats, such as about 10-15 beats, or over a specified time interval, such as about 5 to 15 seconds. In one embodiment, measurement circuit 610 measures only sensed (intrinsic) R-R interval for determining the R-R variability, as low R-R variability when resulting from pacing may confound atrial tachyarrhythmia detection or discrimination. In one embodiment, measurement circuit 610 measures the heart sound amplitude being an amplitude of a heart sound of the at least one specified type heart sounds detected by heart sound detector 608 for each beat detected by beat detector 606. In various embodiments, measurement circuit 610 measures S1 amplitude being an amplitude of the S1 detected for each beat, S2 amplitude being an amplitude of the S2 detected for each beat, and/or S3 amplitude being an amplitude of the S3 detected for each beat. In one embodiment, measurement circuit 610 measures the diastolic interval and the systolic interval. The diastolic is the time interval between the detected S2 and the subsequently detected R-wave in each beat (i.e., S2-R interval). The systolic interval is the time interval between the detected R-wave to the subsequently detected S2 in each beat (i.e., R-R2 interval). Atrial tachyarrhythmia detector 612 detects one or more specified types of atrial tachyarrhythmia using the measured parameters. In various embodiments, tachyarrhythmia detector 612 is configured to perform various detection methods as discussed below with reference to FIGS. 8-10.

In various embodiments, the patient heart rate can be detected using any cardiac signal indicative of the patient's cardiac cycles, and the heart sounds can be detected using a sensor capable of sensing the heart's mechanical vibrations. In various embodiments, system 600 is part of a CRM system that includes an implantable medical device that allows for sensing of the cardiac signal and the heart sounds using an implantable acoustic sensor housed in or coupled to the implantable medical device, as further discussed below with reference to FIGS. 11 and 12. However, the present subject matter is not limited to applications using an implantable medical device.

In various embodiments, the circuit of system 600, including its various elements discussed in this document, is implemented using a combination of hardware and software (including firmware). In various embodiments, beat detector 606, heart sound detector 608, measurement circuit 610, and/or atrial tachyarrhythmia detector 612 may each be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 7:
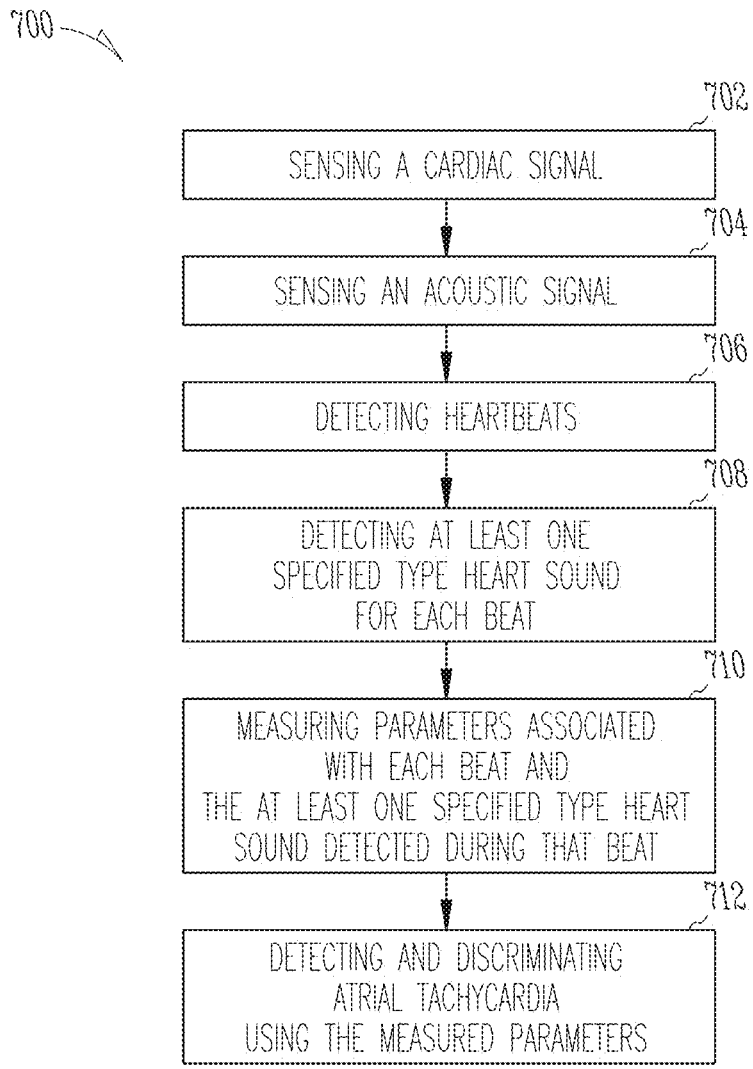
FIG. 7 is a flow chart illustrating an embodiment of a method for detecting and discriminating atrial tachycardia using heart sounds.

FIG. 7 is a flow chart illustrating an embodiment of a method 700 for detecting and discriminating atrial tachycardia using heart sounds. In one embodiment, system 600 is configured to perform method 700.

At 702, a cardiac signal indicative of heartbeats is sensed. The cardiac signal may be any cardiac signal that is indicative of a patient's cardiac cycles, such as surface ECG, subcutaneous ECG, and intracardiac electrogram. At 704, an acoustic signal indicative of heart sounds is sensed. The acoustic signal is indicative of mechanical vibrations of the patient's heart, such as an accelerometer signal or a microphone signal. At 706, the heartbeats are detected using the cardiac signal. At 708, at least one specified type heart sound is detected for each detected beat of the heartbeats. In one embodiment, heart sounds are detected using ensemble averaging, in which the acoustic signal is ensemble-averaged before the at least one specified type heart sound is detected. The detected heart sounds each correspond to a detected heart beat to allow for measurement of parameters at 710. In another embodiment, at least one specified type heart sound is detected during each detected beat of the heartbeats at 708, without ensemble averaging. At 710, parameters associated with each detected beat and the heart sound(s) detected during that detected beat are measured. Examples of such parameters include the heart rate, the R-R variability, the one or more heart sound amplitudes, the systolic interval, and the diastolic interval as discussed above. At 712, atrial tachycardia is detected and discriminated using the measured parameters. Examples illustrating how step 712 is performed are discussed below with reference to FIGS. 8-10.

In one embodiment, method 700 is performed using an implantable medical device, which may include or coupled to an implantable acoustic sensor to sense the acoustic signal. In various embodiments, method 700 may be performed using a system with implantable components, external (non-implantable) components, or a combination of implantable and external components. In various embodiments, the detection of the specified type atrial tachyarrhythmia is used for diagnostic and/or therapy control purposes. For example, detection of AF may be used for determining AF burden in a heart failure patient for purposes such as titrating AF and/or heart failure therapies for that patient.

Figure 8:
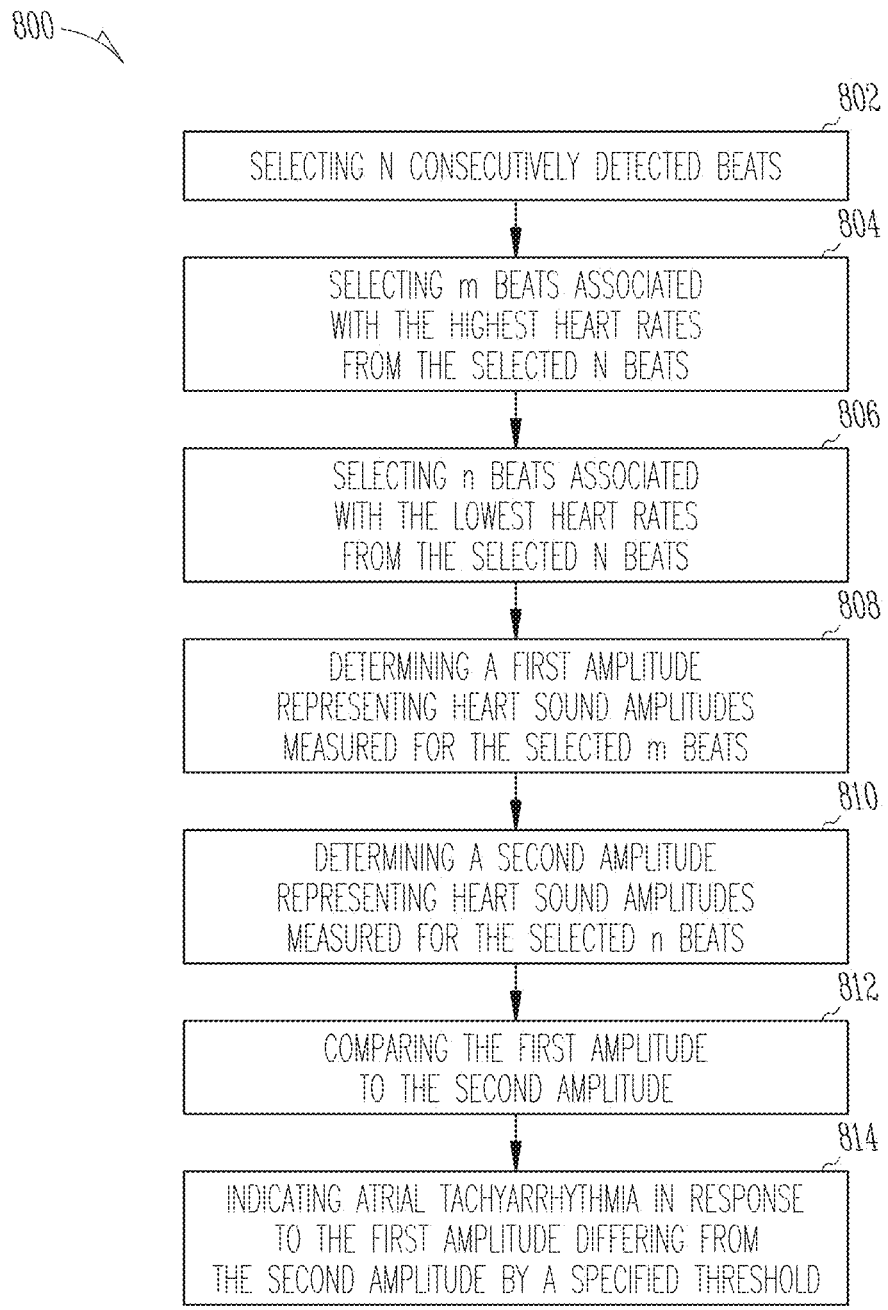
FIG. 8 is a flow chart illustrating an embodiment of a method for detecting atrial tachyarrhythmia using heart rate and heart sound amplitude.

FIG. 8 is a flow chart illustrating an embodiment of a method 800 for detecting atrial tachyarrhythmia using heart rate and heart sound amplitude. Method 800 is an example of part of step 712 of method 700. In one embodiment, atrial tachyarrhythmia detector 612 is configured to perform method 800. To perform method 800, measurement module 610 is configured to measure at least the heart rate and heart rate amplitudes for at least one specified type heart sounds. Atrial tachyarrhythmia detector 612 is configured to detect at atrial tachyarrhythmia using the measured heart rate and heart sound amplitude.

At 802, N beats are selected. The N beats are consecutively detected beats of the heartbeats, where N is a specified number. In one embodiment, N is chosen based on balance between speed and reliability of atrial tachyarrhythmia detection, as a large N may reduce false detection but miss short episodes of atrial tachyarrhythmia. At 804, m beats associated with the highest heart rates is selected from the selected N beats. At 806, n beats associated with the lowest heart rates are from the selected N beats. The numbers in and n can be predetermined and can be equal or different numbers. At 808, a first amplitude is determined. The first amplitude represents the heart sound amplitudes measured for the selected m beats. At 810, a second amplitude is determined. The second amplitude represents the heart sound amplitudes measured for the selected n beats. In one embodiment, the first and second amplitudes are determined using ensemble average of the heart sound amplitudes. At 812, the first amplitude is compared to the second amplitude. At 814, detection of atrial tachyarrhythmia is indicated in response to the first amplitude differing from the second amplitude by a specified threshold.

In one embodiment, S1 amplitude is used for the atrial tachyarrhythmia detection. At 808, a first S1 amplitude representing the S1 amplitudes measured fir the selected m beats is determined. At 810, a second S1 amplitude representing the S1 amplitudes measured for the selected n beats is determined. At 812, the first S1 amplitude is compared to the second S1 amplitude. At 814, detection of atrial tachyarrhythmia is indicated in response to the second S1 amplitude being higher than the first S1 amplitude by a specified first threshold.

In one embodiment, S2 amplitude is used for the atrial tachyarrhythmia detection. At 808, a first S2 amplitude representing the S2 amplitudes measured for the selected m beats is determined. At 810, a second S2 amplitude representing the S2 amplitudes measured for the selected n beats is determined. At 812, the first S2 amplitude is compared to the second S2 amplitude. At 814, detection of atrial tachyarrhythmia is indicated in response to the second S2 amplitude being higher than the first S2 amplitude by a specified second threshold.

In one embodiment, S3 amplitude is used for the atrial tachyarrhythmia detection. At 808, a first S3 amplitude representing the S3 amplitudes measured for the selected m beats is determined. At 810, a second S3 amplitude representing the S3 amplitudes measured for the selected n beats is determined. At 812, the first S3 amplitude is compared to the second S3 amplitude. At 814, detection of atrial tachyarrhythmia is indicated in response to the first S3 amplitude being higher than the second S3 amplitude by a specified third threshold.

In the illustrated embodiment, m and n beats, which are associated with the highest and lowest heart rates, respectively, are selected from the selected N beats and placed into two groups. This represents a specific example of method 800. In various embodiments, the N beats can be placed into X groups in descending order of the heart rate, which X is an integer between 2 and N. The heart sound amplitudes (S1, S2, and/or S3 amplitudes) are determined for each group of the X groups. The detection of atrial tachyarrhythmia is based upon trend of changes in the heart sound amplitudes across the X groups. An extreme case would be X=N, in which all of the N beats are sorted by the heart rate from high to low (in descending order). The heart sound amplitudes are determined for each beat. A trend of the heart sound amplitude across the sorted N beats is obtained (for example by a linear fit), and atrial tachyarrhythmia is declared if the slope of the trend is positive for S1 amplitude, positive for S2 amplitude, and/or negative for S3 amplitude.

In various embodiments, any one or more of the S1 amplitude, S2 amplitude, and S3 amplitude can be used for the atrial tachyarrhythmia detection. When more than one type of heart sound is specified, detection of atrial tachyarrhythmia can be indicated by majority voting. In one embodiment, weighting factors are applied to heart sound types before the detection of atrial tachyarrhythmia can be indicated by voting. The weighting factors can be determined based on the confidence levels associated with using S1 amplitude, S2 amplitude, and S3 amplitude in the detection of atrial tachyarrhythmia.

Figure 9:
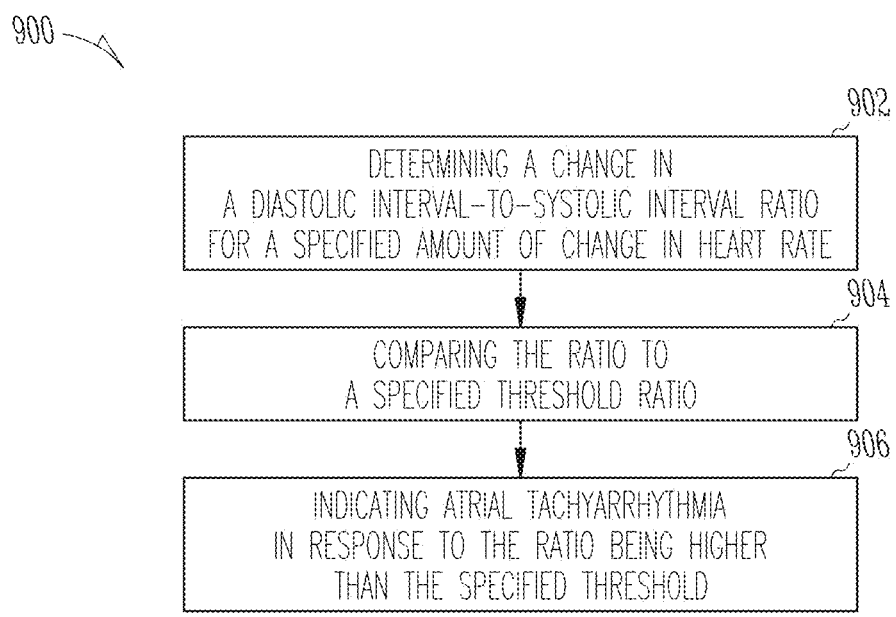
FIG. 9 is a flow chart illustrating an embodiment of a method for detecting atrial tachyarrhythmia using diastolic and systolic intervals.

FIG. 9 is a flow chart illustrating an embodiment of a method 900 for detecting atrial tachyarrhythmia using diastolic and systolic intervals. Method 900 is an example of part of step 712 of method 700. In one embodiment, atrial tachyarrhythmia detector 612 is configured to perform method 900. To perform method 900, measurement module 610 is configured to measure at least the heart rate, the diastolic interval, and the systolic interval. Atrial tachyarrhythmia detector 612 is configured to detect atrial tachyarrhythmia using the measured heart rate, diastolic interval, and systolic interval.

At 902, a change in the ratio of the diastolic interval (S2-R interval) to the systolic interval (R-S2 interval) is determined for a specified amount of change in the heart rate (ΔHR). At 904, the ratio (Δ(S2-R interval/R-S2 interval)) is compared to a specified threshold ratio. At 906, detection of atrial tachyarrhythmia is indicated in response to the ratio being higher than the specified threshold.

The illustrated embodiment is discussed above as a specific example of method 900. In various embodiments, one or more time intervals each measured between ft and S1, R and S2, and/or S1 and S2 can be used for detecting atrial tachyarrhythmia based on diastolic and systolic intervals. For example, S2-R interval can be measured as the diastolic interval and compared to a specified threshold interval, and detection of atrial tachyarrhythmia is indicated by impaired filling in response to the S2-R interval being shorter than the specific threshold interval (below which time is insufficient for proper filling). In another embodiment, S2-S1 interval is also measured as the diastolic interval, and S1-S2 interval is also measured as the systolic interval. Atrial tachyarrhythmia can be detected using up to four ratios using the two mechanical intervals (S1-S2 interval and S2-S1 interval) and the two electromechanical intervals (R-S2 interval and S2-R interval).

Figure 10:
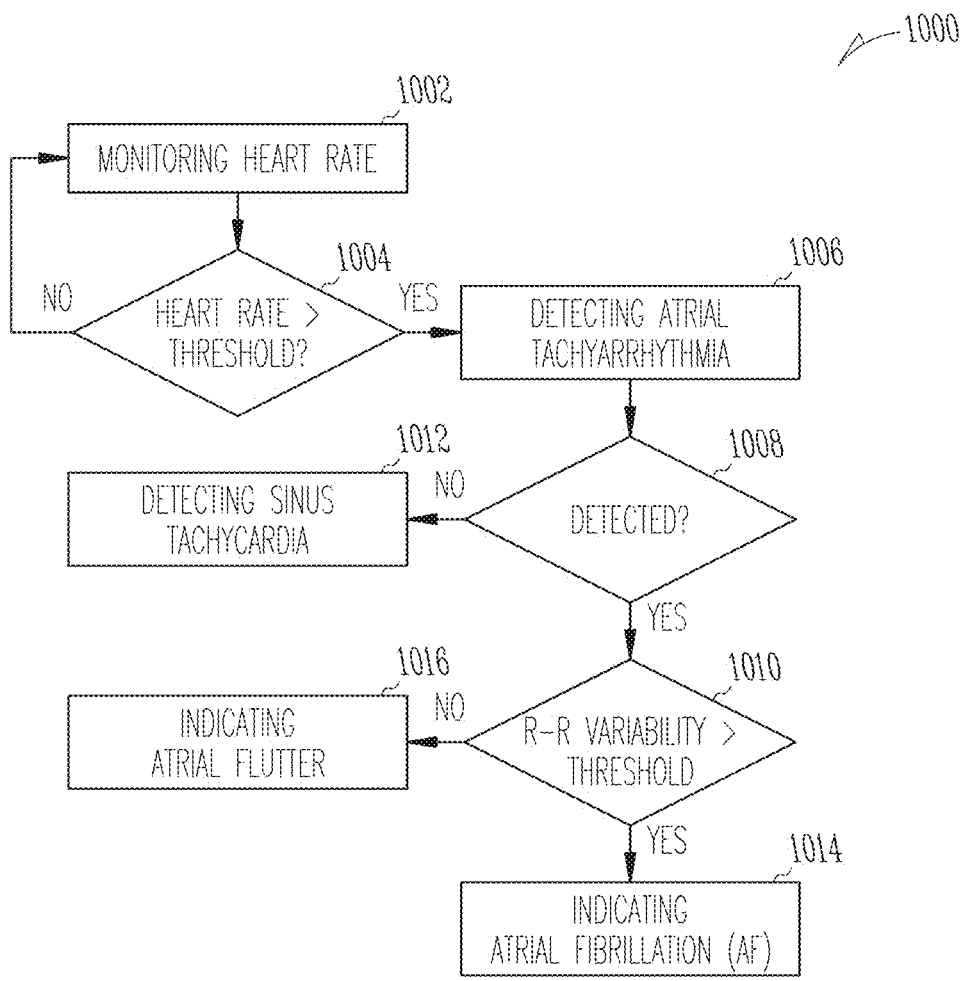
FIG. 10 is a flow chart illustrating an embodiment of a method for discriminating among different types of tachycardia.

FIG. 10 is a flow chart illustrating an embodiment of a method 1000 for discriminating atrial tachycardia. Method 1000 is an example of part of step 712 of method 700. In one embodiment, atrial tachyarrhythmia detector 612 is further configured to perform method 1000, in addition to being configured to perform method 800 or 900. To perform method 1000, measurement module 610 is configured to measure at least the heart rate and the R-R variability. In various embodiments, atrial tachyarrhythmia detector 612 is configured to indicate a plurality of specified types of atrial tachyarrhythmia based on an outcome of performing method 800 or 900.

At 1002, the heart rate is monitored. If the heart rate exceeds a specified threshold heart rate at 1004, atrial tachyarrhythmia is detected at 1006. Examples of a method for performing 1006 include methods 800 and 900. If the atrial tachyarrhythmia is not detected at 1006, sinus tachycardia is detected at 1012. In one embodiment, sinus tachycardia is indicated by the heart rate being higher than the specified threshold heart rate, the R-R variability being not higher than a specified threshold R-R variability, and the S1 amplitude being higher than a specified threshold S1 amplitude (or the S2 amplitude being higher than a specified threshold S2 amplitude, or the S3 amplitude being lower than a specified threshold S3 amplitude).

If the atrial tachyarrhythmia is detected at 1008, it can be discriminated, if necessary or desirable, to determine whether it is AF or atrial flutter based on the R-R variability. If the R-R variability is higher than the specified threshold R-R variability at 1010, AF is indicated at 1014. If the R-R variability is not higher than the specified threshold R-R variability at 1010, atrial flutter is indicated at 1016.

Figure 11:
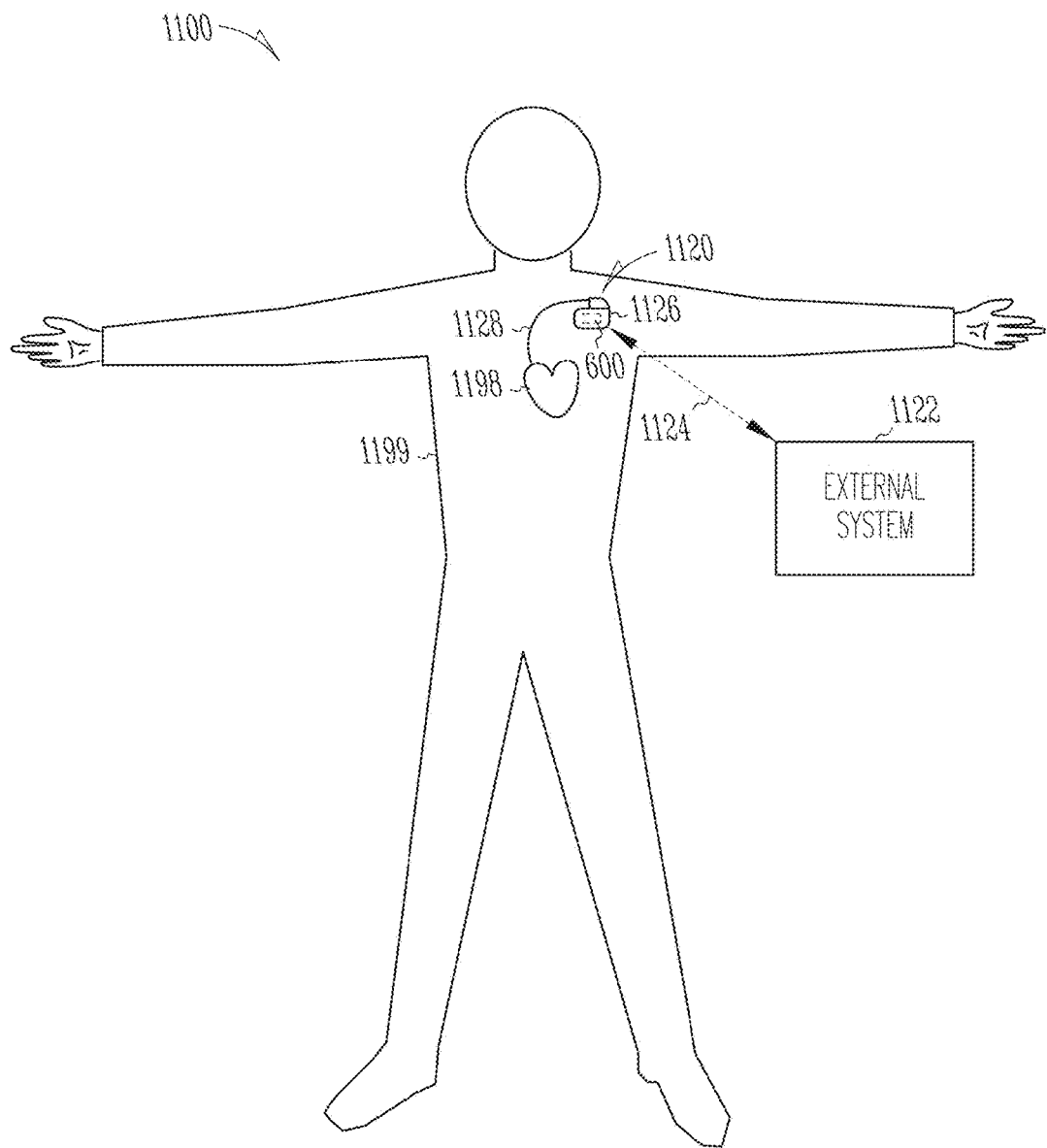
FIG. 11 is an illustration of an embodiment of a cardiac rhythm management system and portions of an environment in which the system operates.

FIG. 11 is an illustration of an embodiment of a cardiac rhythm management (CRM) system 1100 and portions of an environment in which system 1100 operates. System 1100 includes an implantable system 1120, an external system 1122, and a telemetry link 1124 providing for communication between implantable system 1120 and external system 1122.

Implantable system 1120 includes, among other things, implantable medical device 1126 and lead system 1128. In various embodiments, implantable medical device 1126 is an implantable CRM device including one or more of a cardiac monitor, a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device. As illustrated in FIG. 11, implantable medical device 1116 is implanted in a patient's body 1199. In various embodiments, lead system 1128 includes leads for sensing physiological signals and delivering pacing pulses, cardioversion/defibrillation shocks, neurostimulation pulses, pharmaceutical agents, biological agents, and/or other types of energy or substance for treating cardiac disorders. In one embodiment, lead system 1128 includes one or more pacing-sensing leads each including at least one electrode placed in or on the patient's heart 1198 for sensing electrogram and/or delivering pacing pulses. In other embodiments, electrodes placed in body 1199 but away from heart 1198 are used to sense physiological signals and deliver pacing pulses, card shocks, neurostimulation pulses, pharmaceutical agents, biological agents, and/or other types of energy or substance for treating cardiac disorders. In a specific embodiment, one or more electrodes are incorporated onto implantable medical device 1126 for subcutaneous placement.

Implantable medical device 1126 includes system 600 for detecting atrial tachyarrhythmia. In one embodiment, implantable medical device 1126 includes cardiac sensing circuit 602, acoustic sensor 604, beat detector 606, heart sound detector 608, measurement circuit 610, and atrial tachyarrhythmia detector 612. In another embodiment, implantable medical device 1126 includes cardiac sensing circuit 602, beat detector 606, heart sound detector 608, measurement circuit 610, and atrial tachyarrhythmia detector 612, while acoustic sensor 604 includes an acoustic sensor incorporated into lead system 1128 and connected to implantable medical device 1126. In various embodiments, implantable medical device 1126 adjusts the delivery pacing pulses, cardioversion/defibrillation shocks, neurostimulation pulses, pharmaceutical agents, biological agents, and/or other types of energy or substance for treating cardiac disorders in response to one or more types of atrial tachyarrhythmia being indicated by atrial tachyarrhythmia detector 612. For example, implantable medical device 1126 may be configured to deliver CRT or another therapy treating heart failure, determine AF burden being the percentage of time during which AF is indicated by atrial tachyarrhythmia detector 612, and adjust the CRT and/or other therapy based on the AF burden. The other therapy may be delivered by implantable medical device 1126 or using another means associated with or independent of implantable medical device 1126.

In various embodiments, system 600 provides implantable medical device 1126 with the capability of detecting atrial tachyarrhythmia. This eliminates the need to access an atrium for atrial tachyarrhythmia detection when the access is not otherwise required.

External system 1122 allows a user such as a physician or other caregiver or the patient to control the operation of implantable medical device 1126 and obtain information acquired by implantable medical device 1126. In one embodiment, external system 1122 includes a programmer communicating with implantable medical device 1126 bi-directionally via telemetry link 1124. In another embodiment, external system 1122 is a patient management system including an external device communicating with a remote device through a telecommunication network. The external device is within the vicinity of implantable medical device 1126 and communicates with implantable medical device 1126 bi-directionally via telemetry link 1124. The remote device allows the user to monitor and treat the patient from a distant location.

Telemetry link 1124 provides for data transmission from implantable medical device 1126 to external system 1122. This includes, for example, transmitting real-time physiological data acquired by implantable medical device 1126, extracting physiological data acquired by and stored in implantable medical device 1126, extracting therapy history data stored in implantable medical device 1126, and extracting data indicating an operational status of implantable medical device 1126 (e.g., battery status and lead impedance). Telemetry link 1124 also provides for data transmission from external system 1122 to implantable medical device 1126. This includes, for example, programming implantable medical device 1126 to acquire physiological data, programming implantable medical device 1126 to perform at least one self-diagnostic test (such as for a device operational status), and programming implantable medical device 1126 to deliver at least one therapy.

Figure 12:
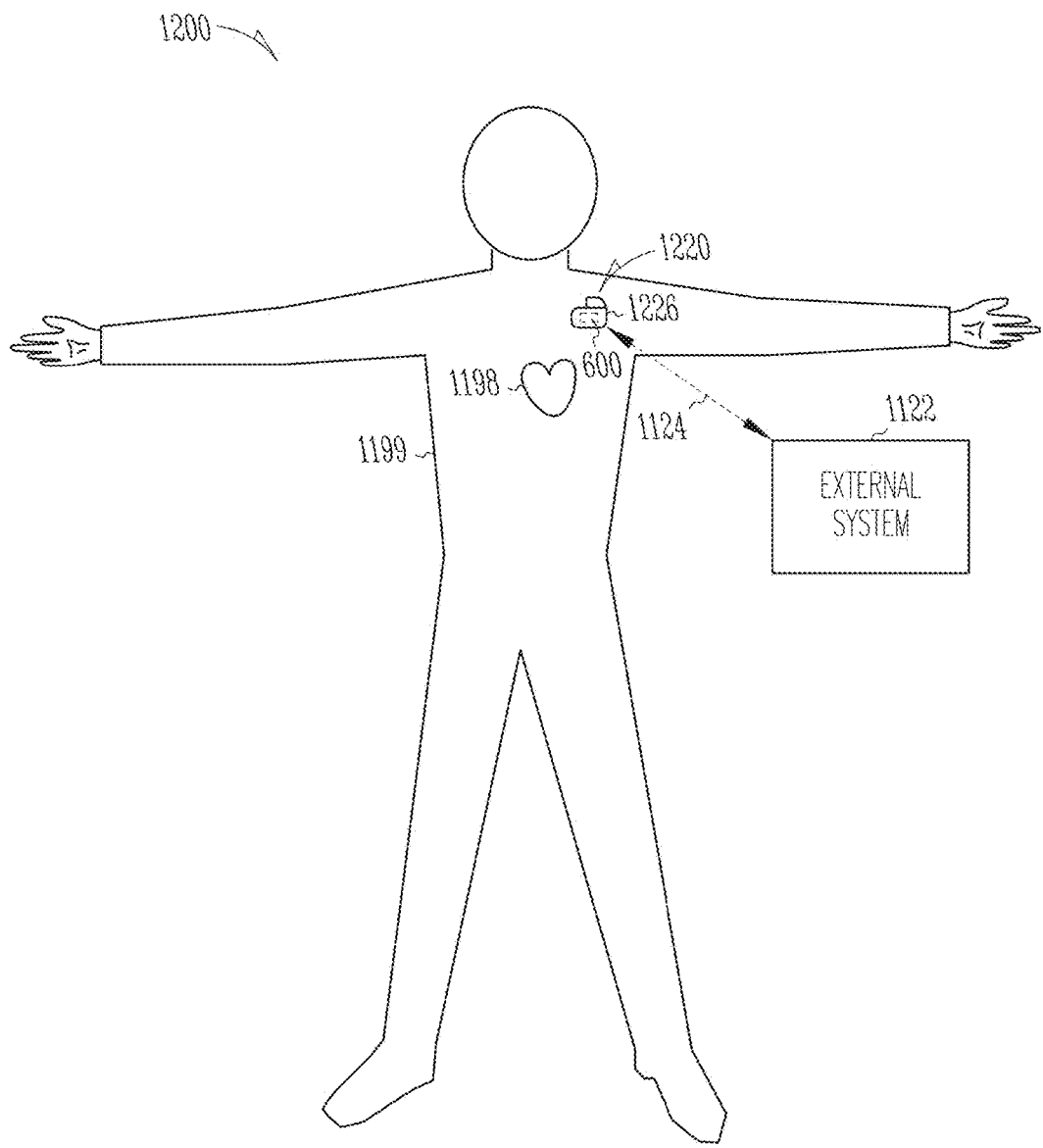
FIG. 12 is an illustration of another embodiment of a cardiac rhythm management system and portions of an environment in which the system operates.

FIG. 12 is an illustration of an embodiment of a CRM system 1200 and portions of an environment in which system 1200 operates. System 1200 includes an implantable system 1220, external system 1122, and telemetry link 1124 providing for communication between implantable system 1220 and external system 1122. Implantable system 1220 differs from implantable system 1120 in that it includes an implantable medical device 1226 without a lead system. Implantable medical device 1220 is a cardiac monitoring device that includes system 600 for the capability of detecting atrial tachyarrhythmia without a lead to provide electrical connection to heart 1198. In various embodiments, implantable medical device 1226 detects atrial arrhythmia and communicates indications of one or more specified types of atrial arrhythmias to external system 1122 via telemetry link 1124 on a continuous or periodic basis or upon request. Such indications provides a physician or other caregiver with information needed for treating the patient. For example, implantable medical device 1226 may be configured to detect AF in a patient with heart failure. Implantable medical device 1226 or external system 1122 may be configured to determine the AF burden, which is then used as a basis for starting, stopping, or adjusting one or more therapies for treating the heart failure.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management system, comprising:
   a cardiac sensing circuit configured to sense a cardiac signal indicative of heartbeats;
   an acoustic sensor configured to sense an acoustic signal indicative of heart sounds;
   a beat detector configured to detect the heartbeats using the cardiac signal;
   a heart sound detector configured to detect at least one specified type heart sound for each beat of the detected heartbeats;
   a measurement circuit configured to measure a heart rate associated with the each beat and a heart sound amplitude being an amplitude of a heart sound of the at least one specified type heart sound detected for the each beat; and
   an atrial tachyarrhythmia detector configured to detect atrial tachyarrhythmia using the measured heart rate and heart sound amplitude.

2. The system of claim 1, wherein the heart sound detector is configured to detect a first heart sound (S1) for the each beat.

3. The system of claim 1, wherein the heart sound detector is configured to detect a second heart sound (S2) for the each beat.

4. The system of claim 1, wherein the heart sound detector is configured to detect a third heart sound (S3) for the each beat.

5. The system of claim 1, wherein the atrial tachyarrhythmia detector is configured to detect the atrial tachyarrhythmia using the heart rates and the heart sound amplitudes measured for a specified number (N) beats of the heartbeats.

6. The system of claim 5, wherein the atrial tachyarrhythmia detector is configured to:
   select N beats being consecutively detected beats of the heartbeats;
   select m beats associated with the highest heart rates from the selected N beats;
   select n beats associated with the lowest heart rates from the selected N beats;
   determine a first amplitude representing the heart sound amplitudes measured for the selected m beats;
   determine a second amplitude representing the heart sound amplitudes measured for the selected n beats;
   compare the first amplitude to the second amplitude; and
   indicate a detection of the atrial tachyarrhythmia in response to the first amplitude differing from the second amplitude by a specified threshold.

7. The system of claim 6, wherein the beat detector is configured to detect R-waves, the measurement circuit is further configured to measure R-R intervals each associated with the each detected beat and determine an R-R variability representing a short-term variability of the R-R intervals, and the atrial tachyarrhythmia detector is configured to discriminate between atrial fibrillation and atrial flutter using the R-R variability in response to the detection of the atrial tachyarrhythmia being indicated.

8. A cardiac rhythm management system, comprising:
   a cardiac sensing circuit configured to sense a cardiac signal indicative of heartbeats;
   an acoustic sensor configured to sense an acoustic signal indicative of heart sounds;

a beat detector configured to detect R-waves using the cardiac signal;

a heart sound detector configured to detect a second heart sound (S2) for each detected R-wave of the detected R-waves;

a measurement circuit configured to measure a heart rate associated with the each detected R-wave and a diastolic interval being a time interval between the detected S2 to the subsequently detected R-wave, and a systolic interval being a time interval between the each detected R-wave to the subsequently detected S2; and an atrial tachyarrhythmia detector configured to indicate a detection of the atrial tachyarrhythmia using the measured heart rate, diastolic interval, and systolic interval.

9. The system of claim 8, wherein the atrial tachyarrhythmia detector is configured to:
   determine a change in a ratio of the diastolic interval to the systolic interval for a specified amount of change in the heart rate;
   compare the ratio to a specified threshold ratio; and
   indicate the detection of the atrial tachyarrhythmia in response to the ratio being higher than the specified threshold.

10. The system of claim 8, wherein the atrial tachyarrhythmia detector is configured to compare the diastolic interval to a specified threshold interval and indicate the detection of the atrial tachyarrhythmia in response to the diastolic interval being shorter than the specified threshold interval.

11. The system of claim 8, wherein the measurement circuit is further configured to measure R-R intervals each associated with the each detected beat and determine an R-R variability representing a short-term variability of the R-R intervals, and the atrial tachyarrhythmia detector is configured to discriminate between atrial fibrillation and atrial flutter using the R-R variability in response to the detection of the atrial tachyarrhythmia being indicated.

12. A method for operating a cardiac rhythm management (CRM) system, comprising:
   sensing a cardiac signal indicative of heartbeats using the CRM system;
   sensing an acoustic signal indicative of heart sounds using an acoustic sensor;
   detecting the heartbeats using the cardiac signal using the CRM system;
   detecting at least one specified type heart sound for each beat of the detected heartbeats using the CRM system;
   measuring parameters using the CRM system, including measuring a heart rate associated with the each beat and a heart sound amplitude being an amplitude of a heart sound of the at least one specified type heart sound detected for the each beat; and
   detecting atrial tachyarrhythmia using the measured heart rate and heart sound amplitude using the CRM system.

13. The method of claim 12, wherein detecting the atrial tachyarrhythmia comprises detecting atrial tachyarrhythmia using the heart rates and the heart sound amplitudes measured for a specified number (N) beats of the heartbeats.

14. The method of claim 13, wherein detecting the atrial tachyarrhythmia comprises:
   selecting N beats being consecutively detected beats of the heartbeats;
   selecting m beats associated with the highest heart rates from the selected N beats;
   selecting n beats associated with the lowest heart rates from the selected N beats;
   determining a first amplitude representing the heart sound amplitudes measured for the selected m beats;
   determining a second amplitude representing the heart sound amplitudes measured for the selected n beats;
   comparing the first amplitude to the second amplitude; and
   indicating a detection of the atrial tachyarrhythmia in response to the first amplitude differing from the second amplitude by a specified threshold.

15. The method of claim 14, wherein detecting the each beat comprises detecting an R-wave of the each beat, and measuring the parameters further comprises measuring R-R intervals each associated with the each detected beat and determining an R-R variability representing a short-term variability of the R-R intervals, and further comprising discriminating between atrial fibrillation and atrial flutter using the R-R variability in response to the detection of the atrial tachyarrhythmia being indicated.

16. The method of claim 12, wherein detecting the each beat comprises detecting an R-wave of the each beat, detecting the at least one specified type heart sound comprises detecting a second heart sound (S2) during the each detected beat, measuring the parameters comprises measuring a heart rate associated with the each detected beat, a diastolic interval being a time interval between the detected S2 to the subsequently detected R-wave in the each detected beat, and a systolic interval being a time interval between the detected R-wave to the subsequently detected S2 in the each detected beat, and detecting the atrial tachyarrhythmia comprises detecting the atrial tachyarrhythmia using the measured heart rate, diastolic interval, and systolic interval.

17. The method of claim 16, wherein detecting the atrial tachyarrhythmia comprises:
   determining a change in a ratio of the diastolic interval to the systolic interval for a specified amount of change in the heart rate;
   comparing the ratio to a specified threshold ratio; and
   indicating a detection of the atrial tachyarrhythmia in response to the ratio being higher than the specified threshold.

18. The method of claim 17, wherein detecting the each beat comprises detecting an R-wave of the each beat, and measuring the parameters further comprises measuring R-R intervals each associated with the each detected beat and determining an R-R variability representing a short-term variability of the R-R intervals, and further comprising discriminate between atrial fibrillation and atrial flutter using the R-R variability in response to the detection of the atrial tachyarrhythmia being indicated.

19. The method of claim 12, wherein measuring the heart sound amplitude comprises measuring one or more of an S1 amplitude being an amplitude of a first heart sound (S1), an S2 amplitude being an amplitude of a second heart sound (S2), and an S3 amplitude being an amplitude of a third heart sound (S3).

20. The method of claim 19, wherein detecting the at least one specified type heart sound for the each beat comprises detecting the at least one specified type heart sound for the each beat using ensemble averaging of the sensed acoustic signal.

* * * * *